United States Patent
Richards et al.

(10) Patent No.: US 6,711,937 B2
(45) Date of Patent: Mar. 30, 2004

(54) HUMIDITY SENSOR FOR INCUBATOR

(75) Inventors: John H. Richards, Warrington, PA (US); Ronald S. Kolarovic, Cinnaminson, NJ (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

(21) Appl. No.: 10/027,496

(22) Filed: Dec. 21, 2001

(65) Prior Publication Data

US 2002/0143232 A1 Oct. 3, 2002

Related U.S. Application Data

(60) Provisional application No. 60/258,011, filed on Dec. 22, 2000.

(51) Int. Cl.[7] .................. G01M 19/00; A61G 11/00
(52) U.S. Cl. .................. 73/29.01; 600/22; 128/1 B; 128/205.26
(58) Field of Search .............. 73/29.01, 29.02, 73/29.05, 25.01; 600/22; 128/1 B, 205.26

(56) References Cited

U.S. PATENT DOCUMENTS

| | | | |
|---|---|---|---|
| 2,721,252 A | 10/1955 | Dorsak | |
| 2,847,546 A | 8/1958 | Crowley et al. | |
| 3,076,451 A | 2/1963 | Stoner | |
| 3,187,744 A | 6/1965 | Dorsak et al. | |
| 3,464,388 A | 9/1969 | Stout | |
| 3,638,926 A | 2/1972 | Melville et al. | |
| 3,782,362 A | 1/1974 | Puzio | |
| 3,821,947 A | 7/1974 | Schossow | |
| 3,854,452 A | 12/1974 | Bardet | |
| 3,987,133 A | 10/1976 | Andra | |
| 4,356,967 A | 11/1982 | Lunick | |
| 4,572,427 A | 2/1986 | Selfridge et al. | |
| 4,701,415 A | 10/1987 | Dutton et al. | |
| 4,750,474 A | 6/1988 | Dukhan et al. | |
| 4,753,758 A | 6/1988 | Miller | |
| 4,796,605 A | 1/1989 | Sasaki et al. | |
| 4,893,508 A | 1/1990 | Friedman | |
| 5,224,923 A | 7/1993 | Moffett et al. | |
| 5,242,375 A | 9/1993 | McDonough | |
| 5,316,542 A | 5/1994 | Koch et al. | |
| 5,330,415 A | 7/1994 | Storti et al. | |
| 5,336,156 A | 8/1994 | Miller et al. | |
| 5,453,077 A | 9/1995 | Donnelly et al. | |
| 5,454,368 A | * 10/1995 | Tarulli ............... | 128/205.26 |
| 5,539,854 A | 7/1996 | Jones et al. | |
| 5,616,115 A | 4/1997 | Gloyd et al. | |
| 5,730,355 A | 3/1998 | Lessard et al. | |
| 5,759,149 A | 6/1998 | Goldberg et al. | |
| 5,792,041 A | 8/1998 | Kobayashi et al. | |
| 5,878,190 A | 3/1999 | Gloyd et al. | |
| 5,897,485 A | * 4/1999 | Koch .............. | 600/22 |
| 5,922,939 A | * 7/1999 | Cota .............. | 73/29.01 |
| 5,957,830 A | 9/1999 | Skulic | |
| 6,014,890 A | * 1/2000 | Breen .............. | 73/29.02 |
| 6,024,694 A | 2/2000 | Goldberg et al. | |
| 6,036,634 A | 3/2000 | Goldberg et al. | |
| 6,256,454 B1 | 7/2001 | Dykes | |
| 6,296,606 B1 | 10/2001 | Goldberg et al. | |

FOREIGN PATENT DOCUMENTS

| | | |
|---|---|---|
| DE | 196 34 338 A1 | 2/1998 |
| JP | 58-103651 | 6/1983 |

* cited by examiner

Primary Examiner—Hezron Williams
Assistant Examiner—Katina Wilson
(74) Attorney, Agent, or Firm—Barnes & Thornburg

(57) ABSTRACT

A sensor module for an incubator or other patient support includes a temperature sensor for sensing the temperature of the air within the interior of the hood of support, a humidity sensor for determining the relative humidity of air drawn from the hood, a temperature sensor for determining the temperature of the air sensed by humidity sensor, and a correlator for adjusting the sensed relative humidity to provide an indication of the relative humidity within the hood.

21 Claims, 10 Drawing Sheets

HUMIDITY SENSOR FOR INCUBATOR

This application claims the benefit of Provisional Application No. 60/258,011, filed Dec. 22, 2000.

BACKGROUND AND SUMMARY OF THE INVENTION

The present invention relates generally to incubators and more particularly to humidity sensors for incubators controlling the humidity of the air within the hood.

It is known to control both the temperature and relative humidity of the air adjacent an infant in an incubator, i.e. the air within the hood. Thermistors for sensing temperature and humidity sensors for sensing relative humidity are known and have been used to provide control signals to controllers for controlling the temperature and relative humidity of the air adjacent an infant in an incubator.

It has been found that when air is drawn from the hood of an incubator past a humidity sensor that the temperature of the air adjacent the humidity sensor may differ significantly from the temperature of the air within the hood of the incubator. Relative humidity is highly temperature sensitive. Thus, when a relative humidity sensor is positioned in locations other than within the hood of the incubator, the sensed relative humidity may be substantially different than the actual relative humidity within the hood of the incubator.

The disclosed humidity sensor correlates the sensed relative humidity to provide a more accurate representation of the relative humidity in the hood.

In an illustrative embodiment, a temperature and humidity sensing module for an infant care enclosure has a portal for receiving air from the enclosure. A primary temperature sensor senses the air received in the module. A humidity sensor is disposed in the module to sense the humidity of the air received therein, and a second temperature sensor within the module determines the temperature of the air at the point the humidity of the air is sensed.

Illustratively, a method for determining the humidity of the air at the position an infant rests in an enclosure is provided, the method comprises the steps of drawing air from the enclosure past a humidity sensor spaced apart from the infant, sensing the temperature of the air drawn from the enclosure, sensing the temperature of the air adjacent the humidity sensor, and correlating the temperature sensed and humidity sensed to determine the humidity adjacent the infant.

Additional features of the invention will become apparent to those skilled in the art upon consideration of the following detailed description of a preferred embodiment exemplifying the best mode of carrying out the invention as presently perceived.

BRIEF DESCRIPTION OF THE DRAWINGS

In describing the illustrative embodiments reference will be made to the drawings in which.

DETAILED DESCRIPTION OF THE DRAWINGS

Incubators and other infant supports configurable as incubators include a base and a hood which combine to form an enclosure within which an infant may be received. Such devices typically include air conditioning systems which, among other things, maintain the oxygen content, relative humidity, flow rate and temperature of air surrounding an infant or baby at appropriate levels. Incubators are well known in the art and are described in Moffett et al., U.S. Pat. No. 5,224,923; McDonough, U.S. Pat. No. 5,242,375; Storti et al. U.S. Pat. No. 5,330,415; Miller et al., U.S. Pat. No. 5,336,156; Lessard et al. U.S. Pat. No. 5,730,355; the disclosures of which are incorporated herein by this reference. A temperature sensing module for an incubator is disclosed in Skulic, U.S. Pat. No. 5,957,830, the disclosure of which is incorporated herein by this reference. An infant support device configurable as an infant radiant warmer and/or an incubator is disclosed in Donnelly et al., U.S. Pat. No. 5,453,077 and Goldberg et al., U.S. Pat. No. 6,296,606, the disclosures of which are incorporated herein by this reference. Incubators and infant support devices configurable as incubators typically include one or more devices for regulating and sensing the air temperature, air flow, oxygen content, and relative humidity in an effort to properly regulate the temperature and health of the infant within the incubator by providing a properly regulated environment surrounding the infant.

Figure 1:
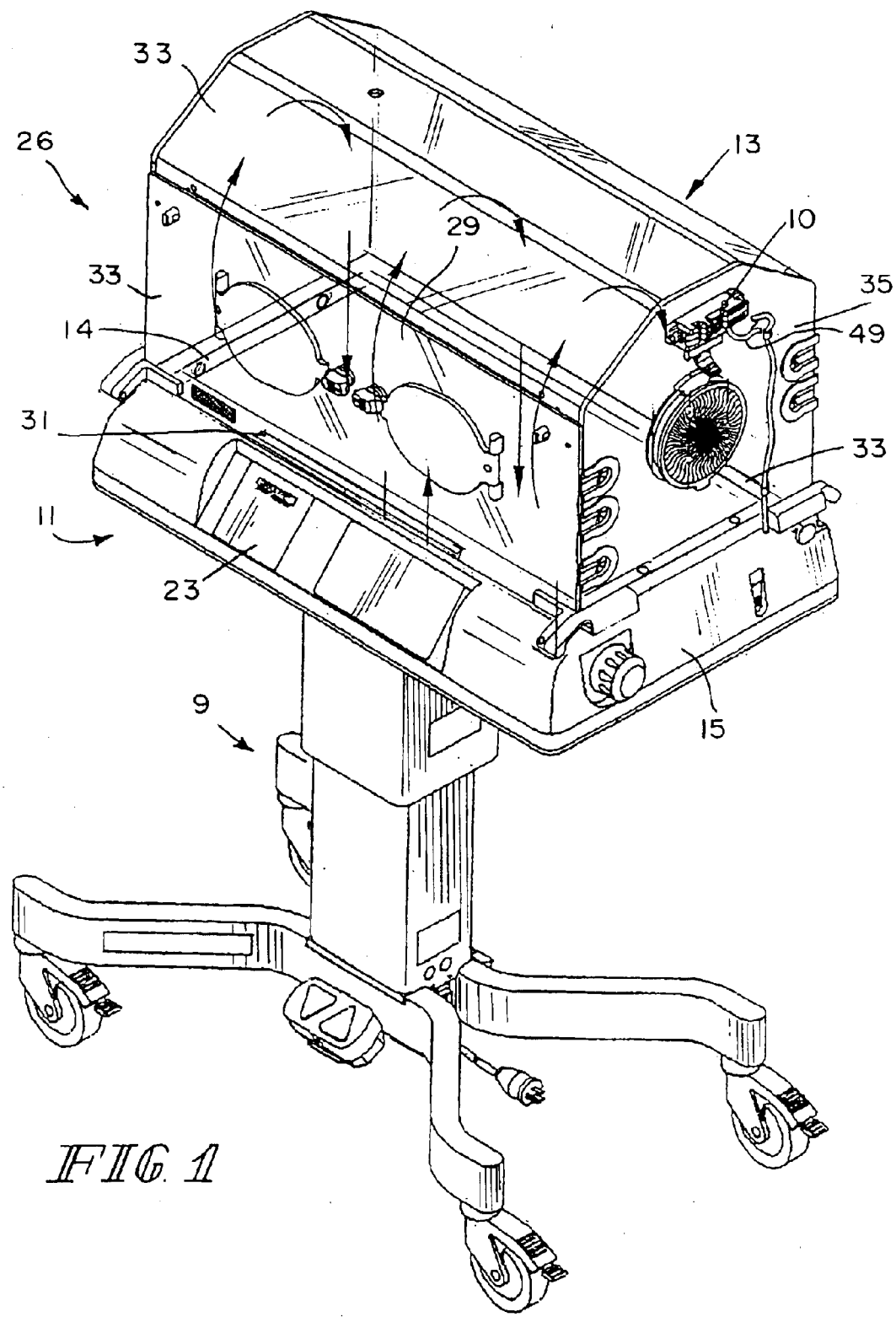
FIG. 1 is a perspective view of an infant incubator having a base, a hood enclosing the base and a sensor module including a humidity sensor extending through a wall of the hood.
Figure 2:
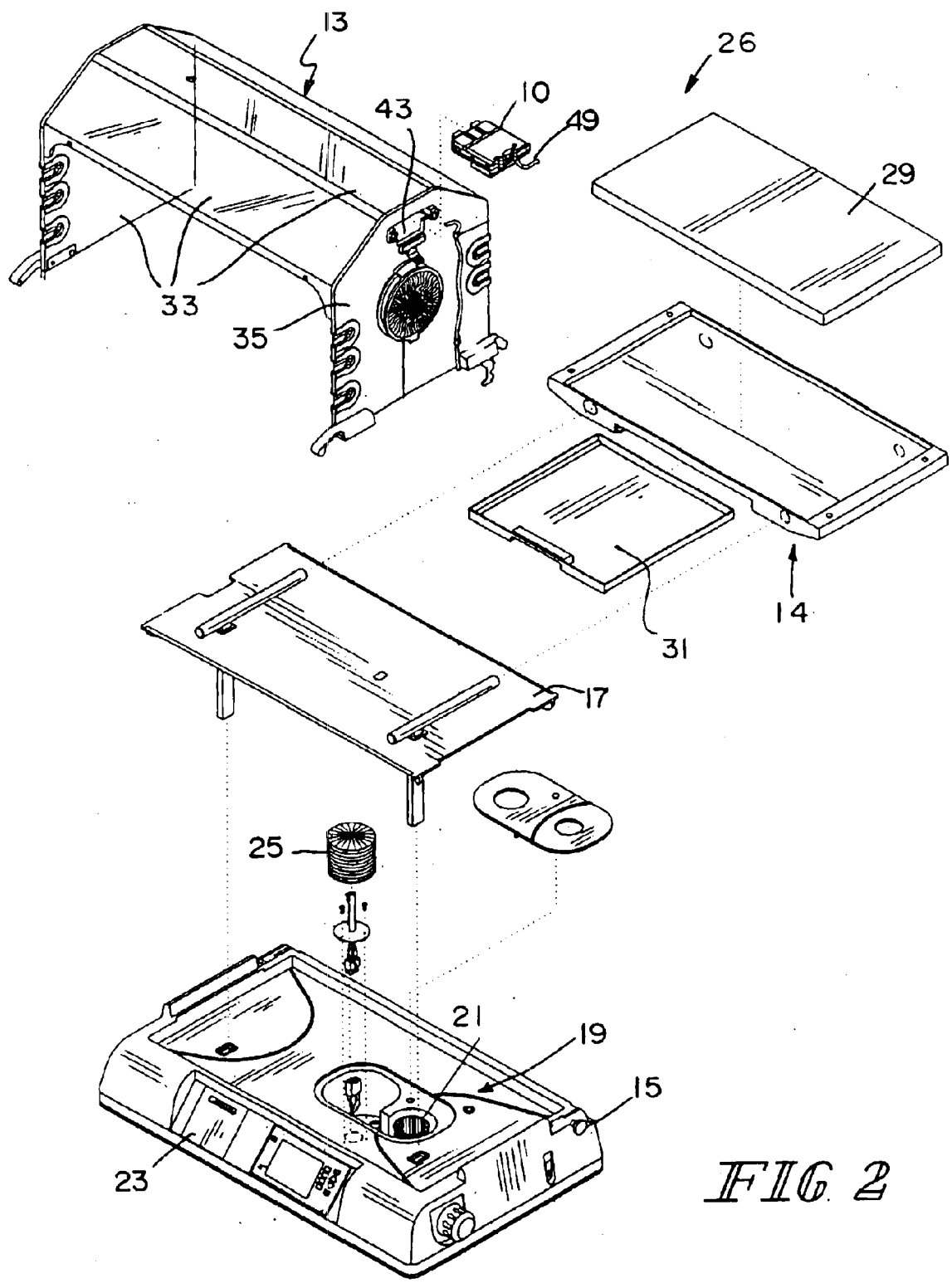
FIG. 2 is an exploded view of the base, hood and sensor module of FIG. 1 with a side wall of the hood removed for clarity.

Referring to FIGS. 1 and 2, the illustrated sensor module 10 is incorporated in an incubator 26 having a base 11 and a hood 13 which combine to form an enclosure within which an infant can be received. Base 11 includes a pedestal 9, a main housing 15 and a deck 17 having an upwardly facing surface. Deck 17 and main housing 15 are configured to provide a plurality of apertures communicating with a below deck ducting 19. Base 11 includes an air conditioning system that includes a fan 21, air filter (not shown), humidifier module 23, oxygen source (not shown) and a heater 25 communicating with below deck ducting 19. The illustrated incubator 26 also includes an in-bed patient scales 14 configured to support a mattress 29 above an x-ray tray 31. As shown in FIGS. 1 and 2, hood 13 includes a plurality of transparent walls 33 formed to include doors and portals for access to an infant held within the enclosure. In the illustrated embodiment, end wall 35 is formed to include a sensor module-receiving aperture 43 within which sensor module 10 is received.

Figure 5:
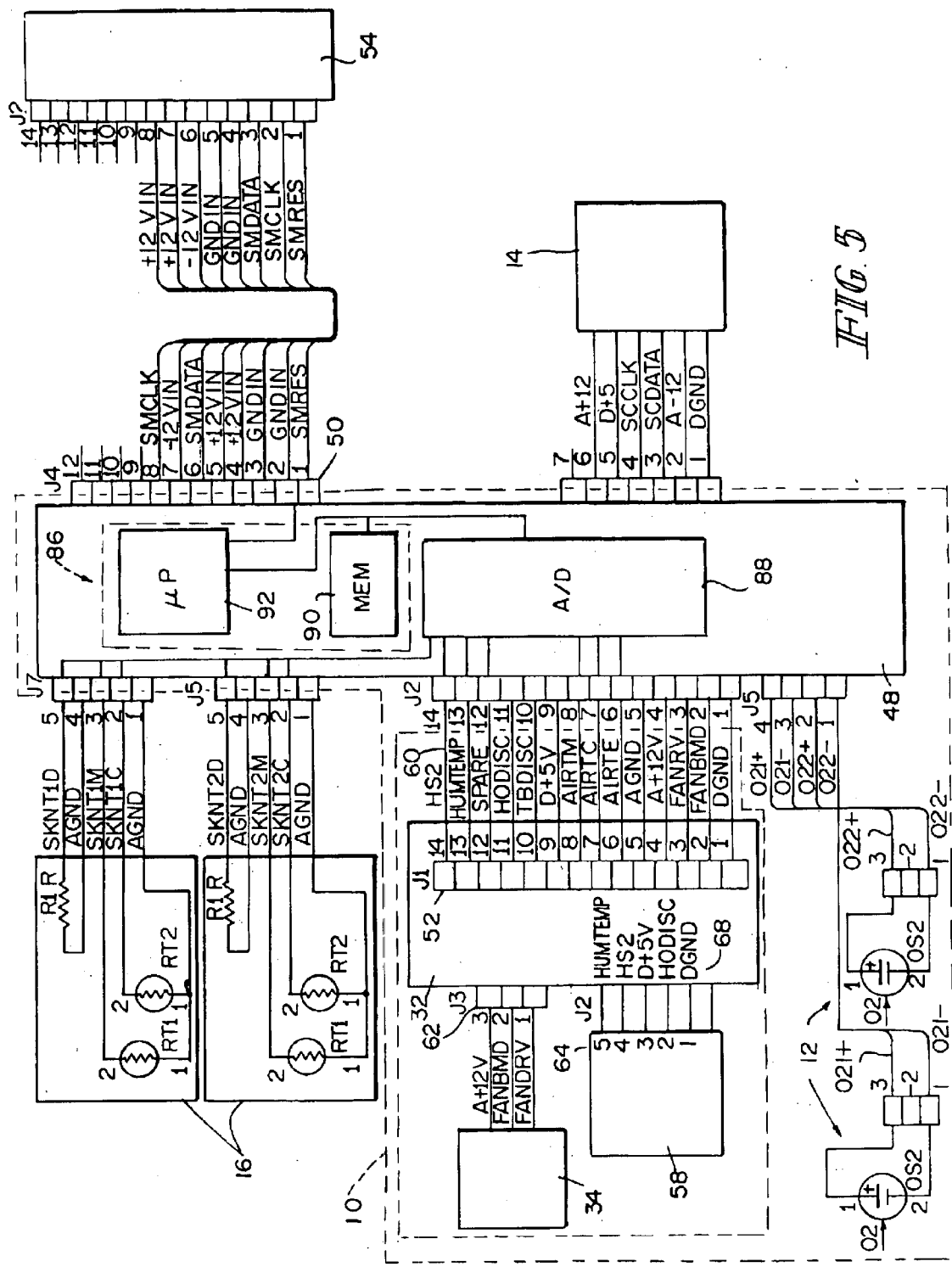
FIG. 5 is a schematic of an incubator sensor module having a main PCB communicating with the humidity sensor module and other sensors, devices and displays including an in-bed scale, a first and second skin probe, and oxygen fuel cells.

The embodiment of sensor module 10 illustrated herein is adapted for use with an incubator 26 which may include other sensors such as oxygen cells 12, scales 14, and skin probes 16 as shown, for example, in FIG. 5. However, it is within the scope of the invention as presently perceived for sensor module 10 to be used in conjunction with an incubator that does not include any of these other sensors or which includes a combination of these other sensors and additional sensors such as photosensors, microphones and the like. It is also within the scope of the invention for sensor module 10 to be used in conjunction with other patient supports including enclosures within which the relative humidity is controlled or sensed.

Figure 3:
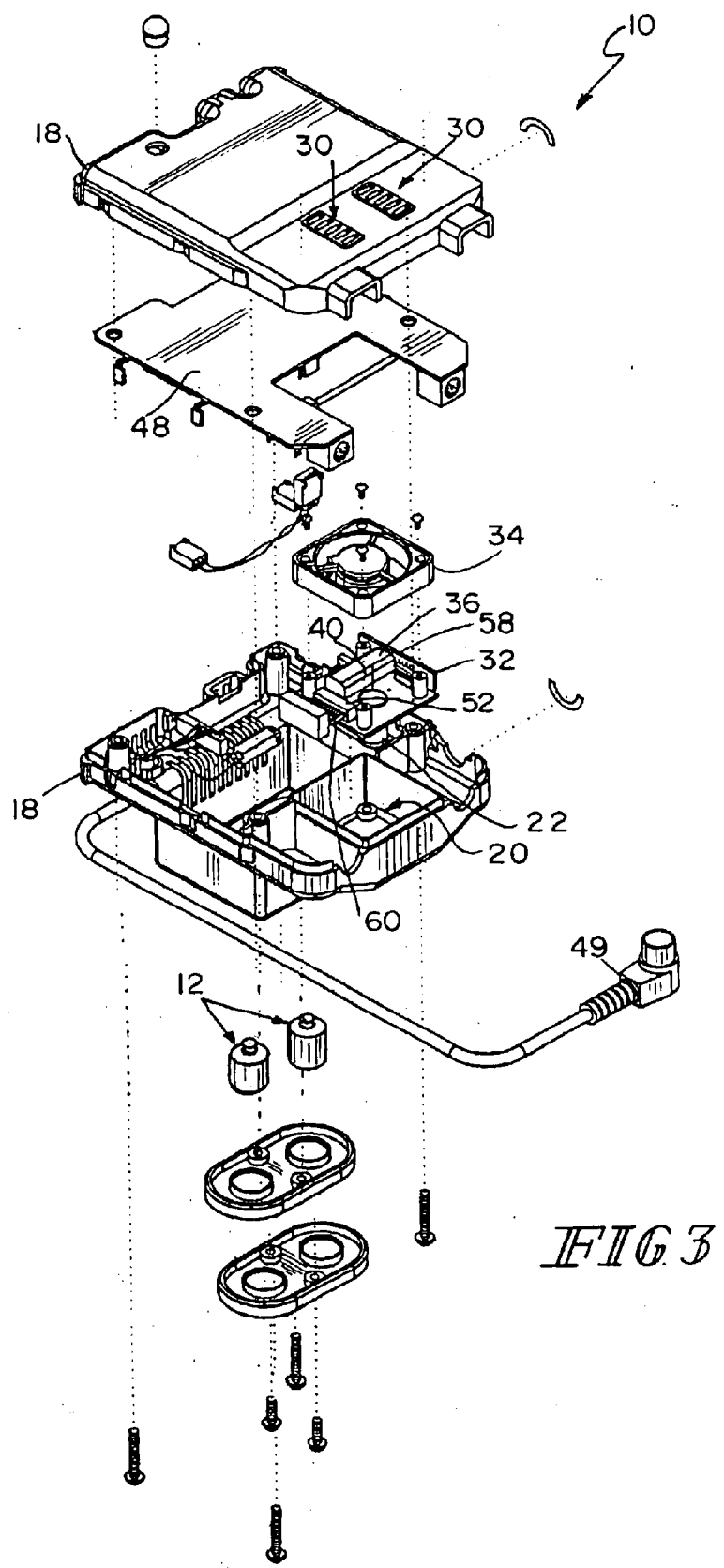
FIG. 3 is an exploded view of the sensor module of FIG. 1.
Figure 4:
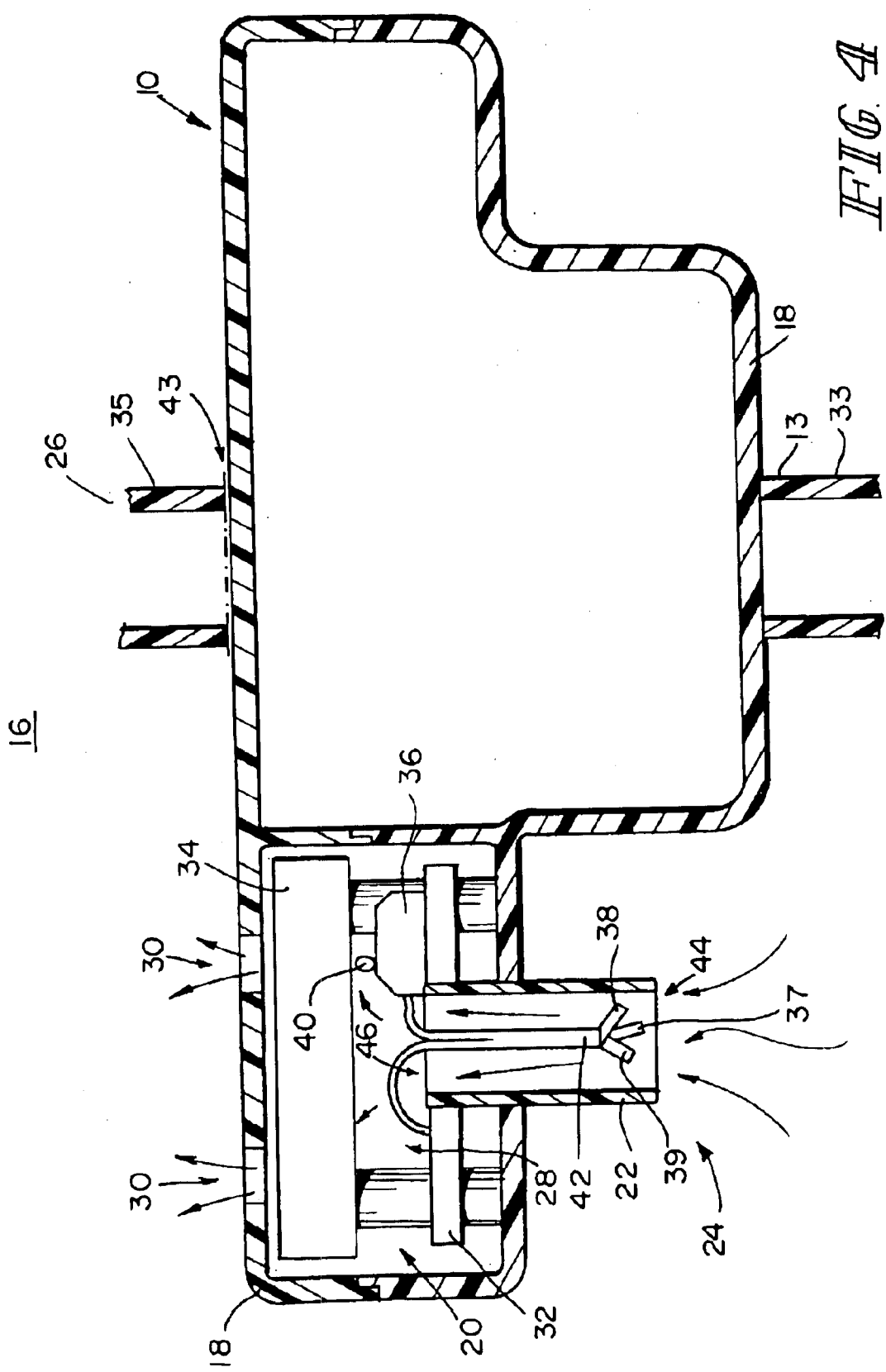
FIG. 4 is a sectional diagrammatic view of the sensor module and a portion of a wall of the hood of FIG. 1 showing a module housing with an air inlet tube through which air within the incubator is pulled by a fan, three air temperature thermistors positioned within the air inlet tube adjacent the inlet opening for sensing the temperature of the air within the hood of the incubator, a humidity sensor mounted to a PCB through which the air inlet tube extends, and a humidity sensor thermistor for sensing the temperature of the air adjacent the humidity sensor.

Sensor module 10 includes a module housing 18, illustratively formed of an upper shell and a lower shell as shown, for example, in FIG. 3. As shown, for example, in FIGS. 1 and 4, sensor module 10 is received in module-receiving aperture 43 so that a portion of module 18 is disposed within interior 24 of hood 13 of incubator 26. Referring to FIGS. 3 and 4, module housing 18 includes a humidity sensing chamber 20 formed to include an air inlet tube 22 providing a portal between the interior 24 of hood 13 of incubator 26 and the interior 28 of humidity sensing chamber 20 of housing 18. Housing 18 is also formed to include air outlet vents 30 providing fluid communication between interior 28 of humidity sensing chamber 20 and interior 24 of hood 13 of incubator 26.

As shown, for example, in FIG. 4, a humidity sensor PCB 32 and a fan 34 are mounted within humidity sensing chamber 20. A humidity sensor 36, a plurality of primary or air temperature sensors or thermistors 37, 38, 39, and secondary (or sensor) air temperature sensor or thermistor 40 are coupled to humidity sensor PCB 32. While the illustrated air temperature sensors 37–40 are described as thermistors, it is within the teaching of the present disclosure for air temperature sensors 37–40 to be any type of temperature transducer capable of sending or modifying a signal indicative of the temperature sensed, such as a semiconductor thermometer, quartz-crystal temperature transducer, or the like.

Illustratively, humidity sensor 36 is mounted via humidity board 58 to humidity sensor PCB 32. Secondary thermistor 40 is mounted adjacent to humidity sensor 36. As used herein with regard to the location of the secondary thermistor, "adjacent to humidity sensor" means being directly on, within or sufficiently close to the humidity sensor so that the temperature of the air sensed by the temperature sensor is substantially equivalent to the temperature of the air being sensed by the humidity sensor 36. Primary thermistors 37, 38, 39 are mounted to a thermistor support wire 42 extending through air inlet tube 22 to position primary thermistors 37, 38, 39 adjacent the incubator opening or inlet port 44 in air inlet tube 22. While the illustrated embodiment of sensor module 10 includes three primary temperature sensors 37–39 which have their readings combined to provide an indication of air temperature in the hood 13 of incubator 26, it is within the scope of the invention as presently perceived to provide a single primary temperature sensor or a plurality of primary temperature sensors. It is also within the scope of the invention as presently perceived for a primary temperature sensor to be positioned at any location that permits accurate sensing of the temperature of the air in the interior 24 of hood 13 of incubator 26 surrounding an infant located therein.

Fan or blower 34 is positioned to draw air from interior 24 of incubator 26 through incubator opening 44 of air inlet tube 22, past primary thermistors 37, 38, 39 and through chamber opening 46 of air inlet tube 22 into humidity sensing chamber 20. The air is also drawn past secondary thermistor 40 and humidity sensor 36 and expelled through outlet vents or exhaust port 30.

It has been found that there may exist a temperature differential between the air in interior 24 of incubator 26 and the air adjacent humidity sensor 36. Applicant has found temperature differential readings as high as four degrees Celsius (7.2° F.) between the air in the interior 24 of incubator 26 and the air adjacent humidity sensor 36. Since relative humidity is highly dependent on air temperature, the relative humidity measured adjacent humidity sensor 36 is different than the relative humidity in interior 24 of incubator 26 if the aforementioned temperature differential exists.

The illustrated sensor module 10 provides an indication of the temperature of the air in the interior 24 of the incubator 26 as well as an indication of the temperature of the air adjacent the humidity sensor 36. Primary thermistors 37, 38, 39 are positioned adjacent interior 24 of incubator 26 and thus provide a relatively accurate indication of the temperature of the air in interior 24 of incubator 26. Primary thermistors 37, 38, 39 also provide a relatively accurate indication of the temperature of air surrounding an infant in incubator 26. Those skilled in the art will recognize that the illustrated primary thermistors 37, 38, 39 do not necessarily provide exact readings of the temperature of the air adjacent the infant because of the physical displacement of the thermistors 37, 38, 39 from the infant and temperature differentials of air within hood 13. It is within the scope of the disclosure for primary thermistors 37, 38, 39 to be calibrated to provide a more accurate indication of the air temperature adjacent the infant. Secondary thermistor 40 provides an accurate indication of the air temperature adjacent humidity sensor 36 because it is located adjacent to humidity sensor 36. In illustrative embodiments, secondary thermistor 40 is mounted directly over an intake opening 84 in humidity sensor 36, as shown, for example, in FIGS. 8 and 9. It should be understood that thermistor 40 may be mounted to be positioned within opening 84 or at a slight distance from humidity sensor 36.

Known mathematical models exist that relate relative humidity to air temperature. Therefore, since sensor module 10 provides an indication of the relative humidity ($RH_{sensor}$) of the air adjacent humidity sensor 36, an indication of the air temperature ($T_s$) adjacent humidity sensor 36 (from secondary thermistor 40), and an indication of the air temperature ($T_h$) in interior 24 of hood 13 of incubator 26 (from primary sensors 37–39), a known model may be applied to determine the relative humidity ($RH_{hood}$) of the air surrounding an infant held within incubator 26.

As shown, for example, in FIGS. 1 and 5, sensor module 10 includes sensor module main PCB 48 coupled via cable 49 to a system host 54. Sensor module 10 may be incorporated into an incubator 26 having other sensors and devices such as skin probes 16, oxygen fuel cells 12, and in-bed scales 14, as shown, for example in FIGS. 3 and 5. It will be understood that sensor module 10 may also be incorporated into incubators and infant support devices having other devices and sensors in addition to the illustrated devices and sensors, other combinations of the illustrated and non-illustrated devices and sensors or no other devices or sensors within the teaching of the disclosure.

In the illustrated embodiment, sensor module main PCB 48 is coupled through a 12-pin single in-line connector 50 via cable 49 to host system 54. In the illustrated embodiment, a sensor module clock signal is present on pin 8 of connector 50, a sensor module data signal is present on pin 6 of connector 50, a sensor module reset signal is carried on pin 1 of connector 50 and power at twelve volts above and below ground potential is provided at pins 2–5 and 7. In the illustrated embodiment, sensor module data is digitally represented by pulses or counts within a given time period measured in sensor module clock cycles having a resolution from 0–1600 counts. Values are assigned to each number of counts based on a range of expected readings. In the illustrated embodiment a relative humidity reading of 0% would be represented by 0 counts, 100% would be represented by 1600 counts, 50% would be represented by 800 counts, 75% would be represented by 1200 counts and so forth.

The sensor module reset signal is used to provide an indication of the nature of the data being transferred by the sensor module main PCB 48 to the system host 54. In the illustrated embodiment, this data can be weight information from the in-bed scale 14, skin temperature information from thermistors of the skin probes 16, air temperature or correlated relative humidity in the interior 24 of incubator 26.

Figure 6:
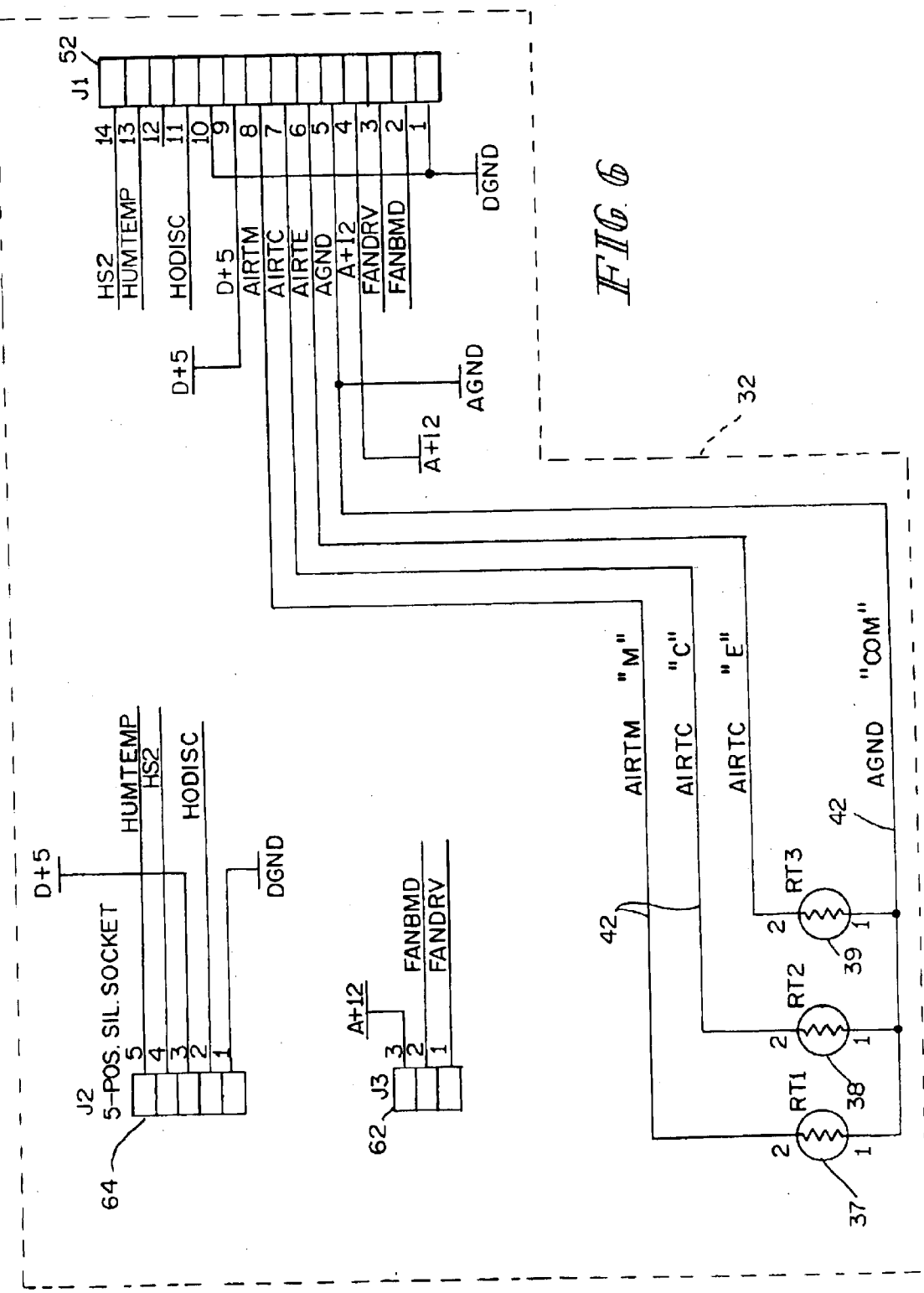
FIG. 6 is a schematic of the humidity sensor module connectors of the incubator system of FIG. 5 showing the configuration of connectors to the Main PCB, a humidity sensor PCB, the fan assembly, and the coupling of the three air temperature thermistors providing "M", "C", and "E" incubator air temperature signals of the humidity sensor module.

Illustratively, sensor module 10 includes humidity sensor PCB 32, fan assembly 34, humidity board 58 and sensor module main PCB 48. In the illustrated embodiment, the raw humidity ($RH_{sensor}$) and temperature ($T_s$, $T_h$) data collected by sensor module 10 is correlated to provide an indication of the relative humidity ($RH_{hood}$) of the air in hood 13 surrounding the infant in the incubator 26 within the module by a correlator contained on sensor module main PCB 48. Thus correlated relative humidity data ($RH_{hood}$) is sent from sensor module main PCB 48 to system host 54. Those skilled in the art will recognize that it is within the scope of the disclosure for correlation to be performed by system host 54 based on raw temperature ($T_s$, $T_h$) and relative humidity ($RH_{sensor}$) data. Therefore, humidity sensor PCB 32 is coupled through a 14-pin dual in-line connector 52 and a ribbon wire 60 with sensor module main PCB 48. As shown in FIGS. 5 and 6, an HS2 signal indicating the relative humidity ($RH_{sensor}$) sensed by humidity sensor 36, a HUMTEMP signal indicating the temperature ($T_s$) of the air adjacent humidity sensor 36 sensed by secondary thermistor 40, and a HODISC signal for enabling and disabling the humidity sensor 36 and thermistor 37–40 outputs are present on pins 14, 13, and 11, respectively, of connector 52. A FANBMD and FANDRV signal are present on pins 2 and 3 respectively of connector 52 to control operation of fan 34 drawing air from incubator 26 through module inlet 22 and past humidity sensor 36. AIRTM, AIRTC, and AIRTE signals from thermistors 37, 38, and 39, respectively, indicating the air temperature ($T_h$) at the inlet 22 to module 10 are present on pins 8, 7, and 6, respectively, of connector 52. A ground and a DC current at 12 volts above ground are present on pins 5 and 4, respectively, of connector 52. Direct current ground is present on pins 1 and 10 and a direct current at 5 volts above ground is present on pin 9 of connector 52.

As shown for example in FIG. 6, in addition to connector 52 for coupling to sensor module main PCB 48, humidity sensor PCB 32 provides couplings for communication with the humidity board 58, fan assembly 34, and thermistors 37–39. As illustrated, for example, in FIG. 4, thermistors 37–39 are coupled through wires 42 directly to humidity sensor PCB 32. Humidity board 58 and fan assembly 34 are coupled through connector 62 to humidity sensor PCB 32. Illustratively, fan connector 62 is a three pin, single in-line socket. Direct current at 12 volts above ground is present on pin 3 of fan connector 62. FANDRV and FANBMD signals are present on pins 1 and 2 respectively of connector 62 to control operation of the fan.

Illustrative humidity board connector 64 is a five pin, single in-line socket. A five volt above ground direct current for operation of humidity sensor 36 is provided between pins 3 and 5 of connector 64. The HS2 signal, indicating the relative humidity ($RH_{sensor}$) sensed by humidity sensor 36, and the HUMTEMP signal, indicating the temperature ($T_s$) of the air adjacent humidity sensor 36 sensed by secondary thermistor 40, are present on pins 4 and 5 respectively of connector 64. The HODISC signal for enabling and disabling the humidity chip and thermistor outputs is present on pin 2 of connector 64. Illustratively connector 64 mates with connector 68, however, it is within the scope of the disclosure for an appropriately configured cable, ribbon wire or other conductive medium to be coupled between connector 64 and connector 68 on humidity board 58.

Figure 7:
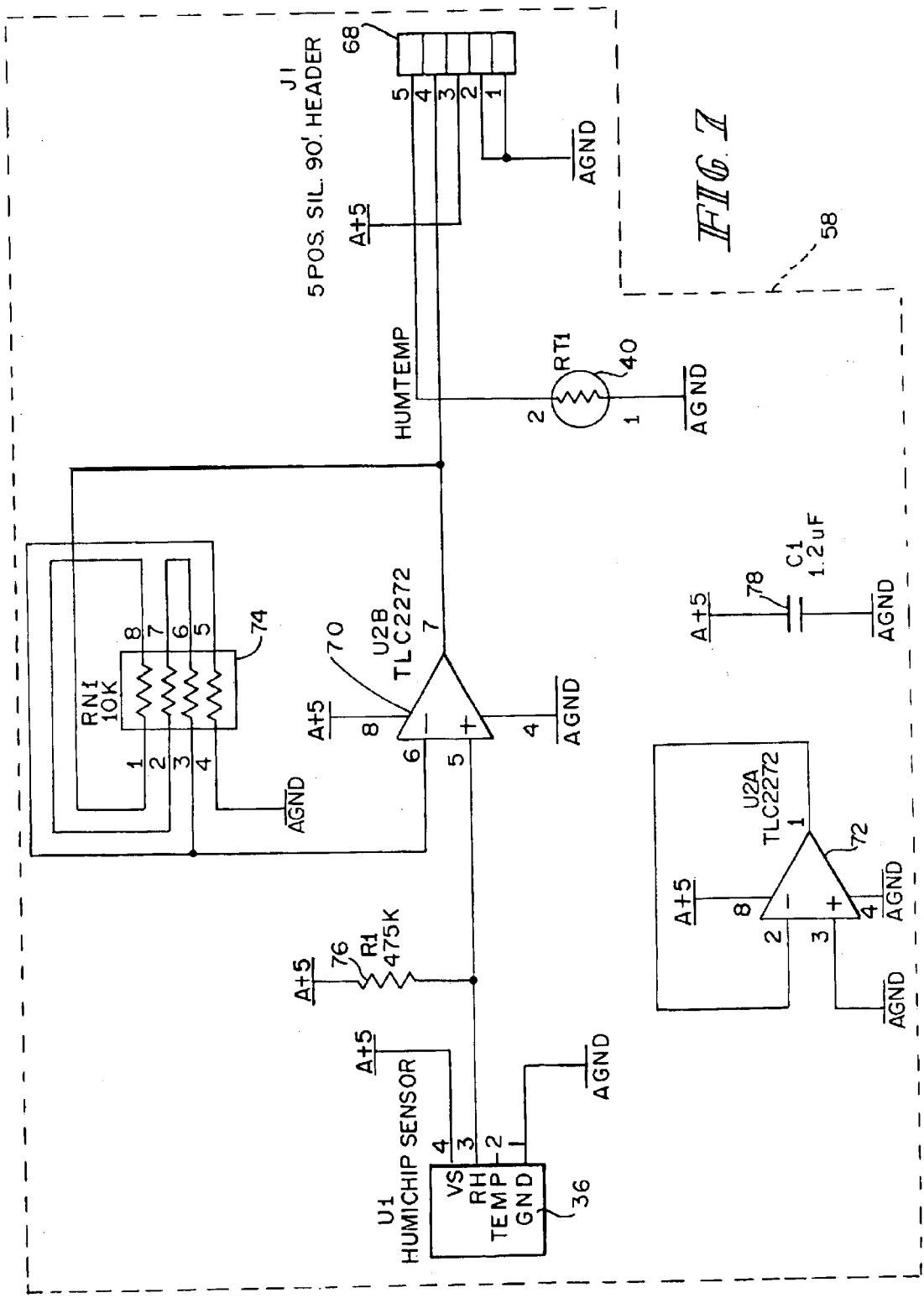
FIG. 7 is schematic of the humidity sensor PCB showing the humidity sensor, humidity sensor thermistor, amplifiers, and feedback resistive network for providing signals indicative of the relative humidity and air temperature at the sensor.

As shown for example, in FIG. 7, humidity board 58 includes humidity sensor 36, two operational amplifiers 70, 72, a resistive network 74, a pull up resistor 76, secondary thermistor 40, filtering capacitor 78, and five pin, single in-line, right-angle connector 68. In FIGS. 6 and 7, lines between components represent traces on humidity sensor PCB 32 and humidity board 58, respectively. Those skilled in the art will recognize that various board trace configurations are within the scope of the invention as presently perceived. As shown, for example, in FIG. 7, power is supplied through pins 1 and 3 of connector 68 which have signals at ground potential and five volts above ground potential present respectively. Pins 1 and 3 are coupled by filtering capacitor 78 to reduce interference. Illustratively, filtering capacitor is a 1.2 uF capacitor. Pin 2 of connector, which caries the HODISC signal is coupled directly to ground so that humidity sensor 36 and thermistor 40 are permanently enabled. Those skilled in the art will recognize that appropriate circuitry could be provided to disable thermistor 40 and humidity sensor 36 when the sensor module 10 is incorporated in an incubator 26 having other functions which might be adversely affected by the constant operation of humidity sensor 36.

As shown, for example, in FIG. 7, the first lead of thermistor 40 is coupled to ground and the second lead of thermistor 40 is coupled to pin 5 of connector 68 to provide the HUMTEMP signal on that pin. Since thermistor 40 is mounted adjacent humidity sensor 36, as shown for example, in FIG. 4, the HUMTEMP signal provides an indication of the temperature ($T_s$) of the air adjacent to humidity sensor 36. Those skilled in the art will recognize that other well known thermoelectric devices capable of providing an indication of air temperature may be substituted for thermistor 40 within the scope of the invention as presently perceived.

Illustratively, humidity sensor 36 is a HumichipSensor™ available from Vaisala Corp., 100 Commerce Way, Woburn, Mass. Humidity sensor 36 includes a ground pin (numbered 1) coupled to ground present on pin 1 of connector 68, and a supply voltage pin (numbered 4) coupled to the five volt above ground direct current signal present on pin 3 of connector 68. A temperature signal pin (numbered 2) on humidity sensor 36 is not used in the illustrated design. A relative humidity signal pin (numbered 3) on humidity sensor 36 is coupled through pull up resistor 76 to the five volts above ground direct current signal available on pin 3 of connector 68 and to the non-inverting input of operational amplifier 70 for amplification to an appropriate signal strength. Illustratively, pull up resistor 76 is a ⅛ watt 475 kOhm resistor having a 1% tolerance.

Illustratively operational amplifier 70 and operational amplifier 72 are each an operative half of an eight-pin dual-operational amplifier chip. Since only operational amplifier 70 is used in the illustrated embodiment, operational amplifier 72 is stilled in accordance with the manufacturer's instructions by coupling the output pin 1 to the inverting input pin 2 and coupling the non-inverting input pin 3 to ground, as shown, for example, in FIG. 7. The shared voltage source pin 8 of operational amplifiers 70, 72 is connected to the five volts above ground direct current signal on pin 3 of connector 68. The shared ground pin 4 of operational amplifiers 70, 72 is connected to the ground signal present on pin 1 of connector 68.

The RH signal output pin 3 of humidity sensor 36 is coupled to non-inverting input pin 5 of operational amplifier 70 which amplifies RH signal to a higher level RS2 signal present on output pin 7 of operational amplifier 70. Output pin 7 of operational amplifier 70 is coupled to pin 4 of connector 68. Output pin 7 is also coupled through three of the resistive elements of resistive network 74 in series to inverting input pin 6 of operational amplifier 70, as shown, for example in FIG. 7. Illustratively, resistive network 74 is a four 10 kOhm eight-pin resistive network. This series coupling of resistive elements of resistive network 74 provides an effective feed back resistance of 30 kOhm. Inverting input pin 6 of operational amplifier 70 is also coupled through one resistive element of resistive network 74 to the ground to provide a pull down resistance of 10 kOhm. Illustratively operational amplifier 70 provides a non-inverted gain of X4 to the RH signal to generate the RS2 signal.

Figure 8:
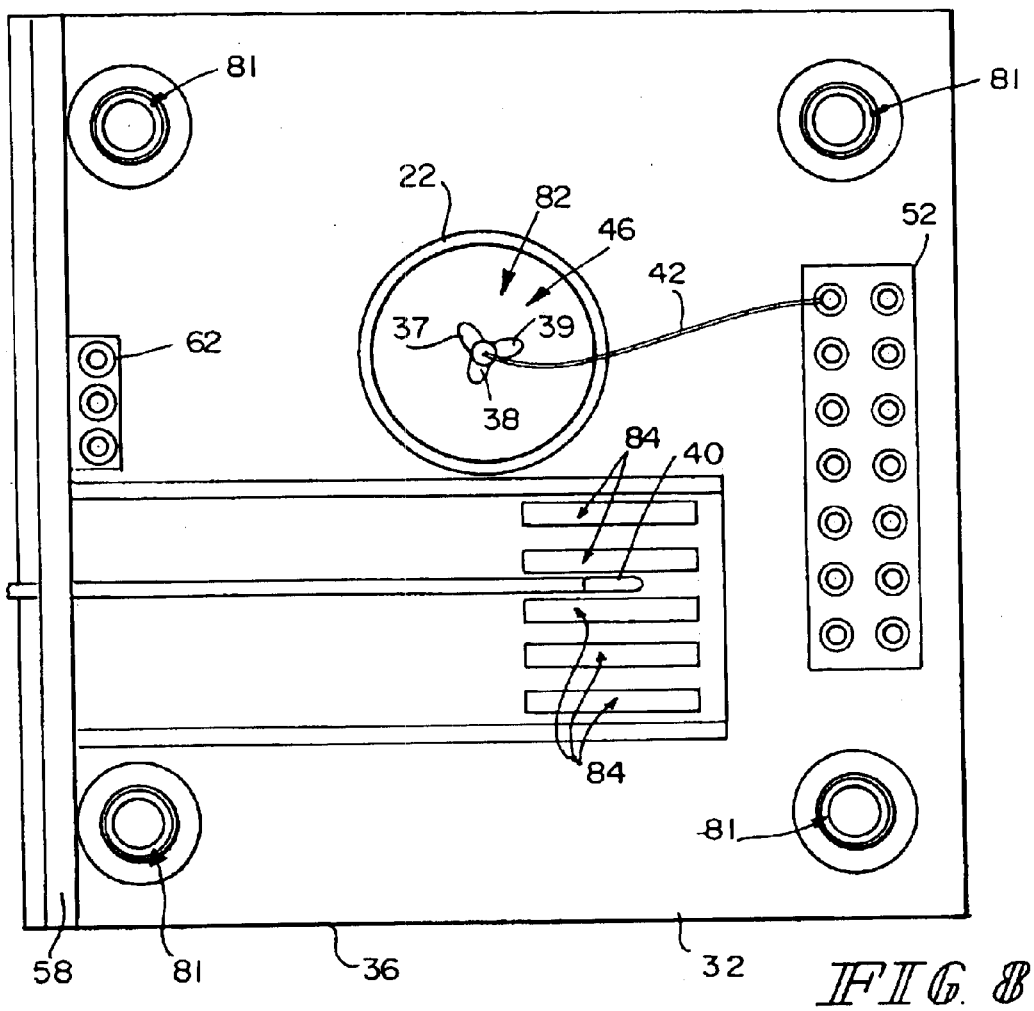
FIG. 8 is a plan view of the layout of the humidity sensor PCB, with the fan removed for clarity, showing the humidity sensor mounted adjacent a central aperture and mounting locations for stand-offs for supporting the fan.
Figure 9:
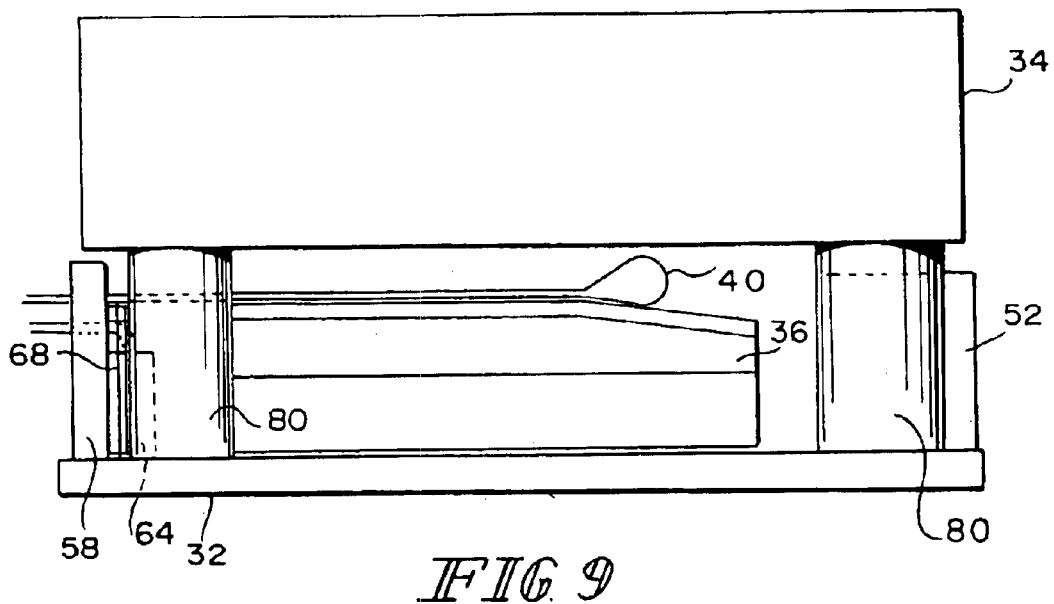
FIG. 9 is a side elevation of the humidity sensor PCB, humidity board, and fan showing the fan mounted on stand-offs connected to the humidity sensor PCB and the humidity board mounted to the humidity sensor PCB with the humidity sensor thermistor mounted adjacent the humidity sensor.

FIGS. 8 and 9 show the humidity sensor PCB 32. Humidity board 58 including humidity sensor 36 is mounted to humidity sensor PCB 32 adjacent a central aperture 82. Inlet tube 22 is mounted in central aperture 82 so that chamber opening 46 is adjacent central aperture 82. Fan 34 (FIG. 9) is mounted by stand offs 80 to mounting locations 81 on humidity sensor PCB 32. Humidity sensor thermistor 40 is mounted adjacent a sensor opening 84 in the humidity sensor 36. Through this configuration, fan 34 pulls internal air from the incubator 26 through inlet 22, past primary thermistors 37-39, through chamber opening 46 at central aperture 82, across secondary thermistor 40 and opening 84 in humidity sensor 36 and expels the air through outlet vents 30.

Relative humidity can be defined as the ratio of the partial pressure of water vapor ($P_{ps}$) of a sample of air to the saturation vapor pressure ($P_{vp}$) at the existing temperature. As an air sample is drawn from the hood 13 of incubator 26 past the primary thermistors 37-39, secondary thermistor 40 and humidity sensor 36, it can be assumed, with the introduction of minimal error, that the partial pressure of water vapor ($P_{ps}$) of the sample remains constant. However, it cannot be assumed that the saturation vapor pressure ($P_{vp}$) of the air remains constant. As was previously explained, it has been found that the temperature of the air sample varies between the inlet 22 and the humidity sensor 36. Saturation vapor pressure is a function of pressure and especially temperature. Several well-known models exist for the saturation vapor pressure of water vapor as a function of temperature, including the Goff-Gratch equation, Clausius Clayperon ("CC") Equation, Bolton Equation, CC equation with L as a function of temperature equation, CC with Constant L equation, and the Modified CC equation. Each of the known equations has its own advantages and limitations. For example, while the Goff-Gratch equation is the most accurate over the broadest range of temperatures, it is also the most complex equation and therefore the most difficult to implement in a correlation mechanism program. The CC with Constant L equation is the least accurate but the easiest to implement in a correlator 86. In the described embodiment, the Modified CC equation is used by the correlator 86 to correlate the measured relative humidity ($RH_{sensor}$) at the humidity sensor 36 to the relative humidity ($RH_{hood}$) of the air within the interior 24 of hood 13 of incubator 26. It is within the scope of the invention as presently perceived to implement the correlator 86 using any known model of relative humidity as a function of temperature. It is also within the scope of the invention to measure values of other dependent variables, such as pressure, for example, at the humidity sensor 36 and within the incubator 26 and to use the measured values in models of relative humidity as a function of temperature and these measured variables.

As previously stated, the illustrated sensor module 10 includes a Vaisala Humichip™ device for relative humidity (RH) measurement. This device outputs 0–1V DC (present on pin 3 as an RH signal) equivalent to 0–100% RH. This signal is in turn gained up X 4 to provide a 0–4V DC signal (identified as HS2 in FIGS. 6 and 7) presented to the sensor module's A/D converter 88. Those skilled in the art will recognize that other humidity sensors may be used within the scope of the disclosure.

When a humidity sensor 36 is located as illustrated in FIG. 4, the sensor measurement of relative humidity ($RH_{sensor}$) includes a rather large error with respect to a reference sensor placed at the inlet port 44 to the sensor module 10. This is because the air temperature ($T_S$) in the vicinity of the sensor 36 is different (higher) than the inlet air temperature ($T_h$). The inlet air stream is locally heated by various components of sensor module 10 when in the vicinity of the humidity chip 36. Thus, although air within the incubator 26 is humidified to a certain RH level, when the air is locally heated in the region of the humidity chip, the RH value decreases. Although the humidity chip 36, when properly calibrated, accurately measures the relative humidity of the air adjacent the chip, this measured relative humidity ($RH_{sensor}$) is lower than the relative humidity ($RH_{hood}$) within the interior 24 of hood 13 of the incubator 26. This effect is due to the change in the saturation vapor pressure ($P_{vp}$) as a result of the localized heating.

Since the discrepancy in measured relative humidity ($RH_{sensor}$) of air in the vicinity of the humidity chip 36 with the actual relative humidity ($RH_{hood}$) of the air in the interior 24 of the hood 13 of incubator 26 results from the temperature differential between the air adjacent the humidity chip 36 and the air in the interior 24 of the incubator 26, the air temperature is measured adjacent the humidity chip 36 and adjacent the interior 24 of the incubator 26. In the illustrated embodiment, these temperatures are measured using thermistors 37–40 positioned in inlet tube 22. It is within the scope of the disclosure to position thermistors 37–39 directly within the interior 24 of hood 13 of incubator 26.

Thermistors are known thermoelectric devices that exhibit varying resistance depending on their temperature. By measuring the resistance of the thermistors 37–40, either directly or indirectly, the temperature of the air adjacent the thermistor 37–40 can be extrapolated. In the illustrated embodiment, the correlator 86 uses digital signals to represent values of temperature ($T_s$, $T_h$) and relative humidity ($RH_{sensor}$, $RH_{hood}$). Therefore, the sensor module 10 converts the measured resistance (in counts) to a temperature value.

In the illustrated embodiment, the resistance to temperature conversion is accomplished using the Steinhart and Hart relationship of:

$$R_t(t) = \exp\left[a_0 + \frac{a_1}{t+273.15} + \frac{a_2}{(t+273.15)^2} + \frac{a_3}{(t+273.15)^3}\right]$$

Where the constants defined for this relationship are:
$a_0 = -2.038519355056$
$a_1 = 1.669953381451 \times 10^3$
$a_2 = 8.130676535890 \times 10^5$
$a_3 = -9.552179931561 \times 10^7$.

The relationship (after simplification) of counts based on thermistor resistance and electrical circuit hardware gain is given as:

$$adc\_counts(thermistor_R) = \frac{273}{4} \cdot \frac{(98 \cdot thermistor_R - 258967)}{(thermistor_R + 9090)}$$

This conversion is appropriately programmed into microprocessor 92 of correlator 86.

The measurement of relative humidity (RH) is a measurement of the ratio of partial pressure of water vapor ($P_{ps}$) to that of the saturation vapor pressure of water ($P_{vp}$), i.e.:

$$RH = \frac{P_{ps}}{P_{vp}}.$$

In the illustrated embodiment of sensor module 10, it is assumed, with the introduction of minimal error, that the same amount of water vapor exists in a given sample of air so that the partial pressure of water ($P_{ps}$) remains constant when the sample is drawn from the incubator interior 24 (or hood 13) to a point adjacent humidity sensor 36. However, because the saturation vapor pressure of water ($P_{vp}$) is highly temperature dependent and the temperature at the hood ($T_h$) is different than the temperature at the sensor ($T_s$), the saturation vapor pressure at the hood ($P_{vph}$) is different from the saturation vapor pressure at the sensor ($P_{vps}$). Since the saturation vapor pressure at the hood ($P_{vph}$) differs from the saturation vapor pressure at the sensor ($P_{vps}$), the relative humidity at the hood ($RH_{hood}$) differs from the relative humidity at the sensor ($RH_{sensor}$). These relative humidities can be expressed:

$$RH_{sensor} = \frac{P_{ps}}{P_{vps}} \text{ and } RH_{hood} = \frac{P_{ph}}{P_{vph}}.$$

When it is assumed that the partial pressure of water vapor does not change between the hood 13 and the sensor 36, i.e. $P_{ph} = P_{ps}$, the above two equations can be simplified and solved for the relative humidity in the interior 24 of the hood 13 of incubator 26 ($RH_{hood}$) as follows:

$$RH_{hood} = RH_{sensor} \cdot \frac{P_{vps}}{P_{vph}}.$$

The humidity chip 36 provides a direct measurement of the relative humidity at the sensor ($RH_{sensor}$) Primary thermistors 37-39 and secondary thermistor 40 provide a measurement of the air temperature at the hood ($T_h$) and sensor ($T_s$), respectively. Given the temperature at a location, the saturated vapor pressure can be determined using known models by properly correlating a measured relative humidity at another location if the temperature at the other location is known. As previously mentioned, the illustrated embodiment uses the Modified Clausius Clayperon Equation ("Modified CC Equation") to determine the saturated vapor pressure at the hood ($P_{vph}$) and the saturated vapor pressure at the sensor ($P_{vps}$) from the hood air temperature ($T_h$) and sensor air temperature ($T_s$) respectively. The modified CC Equation states that the vapor pressure ($P_{vp}$) in millibars at a given temperature (T) is:

$$P_{vp} = e^{\left(53.67957 - \frac{6743.769}{T} - 4.8451\ln(T)\right)}.$$

Thus by providing sensor module 10 with a device capable of providing an indication of relative humidity ($RH_{sensor}$), a device capable of providing an indication of air temperature adjacent the relative humidity device ($T_s$), and a device capable of providing an indication of air temperature in the interior 24 of the hood 13 of incubator 26 ($T_h$), correlator 86 establishes the relative humidity within the hood 13 of incubator 26 ($RH_{hood}$).

In the illustrated embodiment, sensor module 10 is installed in an incubator 26 which also senses and controls other variables. The thermistors 37–40 and humidity sensor 36 of the illustrated embodiment, as well as other sensors for sensing other parameters, generate or affect analog signals indicative of the value of the parameter that they sense. Thus, sensor module 10 includes an analog to digital converter (A/D converter) 88 to convert analog signals indicative of variable parameters into digital signals indicative of variable parameters. Digital signals are typically easier to manipulate under the current state of the electronic art. Nevertheless, it is within the scope of the invention as presently perceived to directly manipulate analog signals indicative of relative humidity ($RH_{sensor}$) at the relative humidity sensor 36 location, temperature ($T_s$) at the relative humidity sensor location, and temperature ($T_h$) in the interior 24 of hood 13 of incubator 26 to establish the relative humidity ($RH_{hood}$) within the interior 24 of hood 13 of incubator 26. It is also within the scope of the invention as presently perceived to use relative humidity sensors and temperature sensors which provide a digital signal indicative of the parameter being measured.

The A/D converter 88 of sensor module 10 is of a known type which upon receipt of an analog signal between zero and five volts provides a digital signal including between 0 and 4095 counts. The data interface between the correlator 86 and the host system 54 accepts and outputs digital data having values between zero and 1600 counts. The digital output of the A/D converter 88 of the sensed relative humidity ($RH_{sensor}$), sensor air temperature ($T_s$), and incubator air temperature ($T_h$) is correlated by correlator 86 to provide a digital signal representative of the incubator relative humidity ($RH_{hood}$). This $RH_{hood}$ is scaled by the correlator 86 using a scaling factor to provide a digital signal having between zero and 1600 counts which is sent to the host system 54. Correlator 86 is illustrated diagrammatically as including memory 90 and a microprocessor 92. In the illustrated embodiment correlation is accomplished using a PIC16C73 8-bit micro-controller integrated circuit including a microprocessor 92 and on board memory 90. In the illustrated embodiment, memory 90 is used to store values of measured parameters such as $RH_{sensor}$, $T_s$, and $T_h$ as well as other parameters measured by other devices 12, 14, 16. These stored values are accessed by microprocessor 92 which is appropriately programmed to calculate $RH_{hood}$ from the stored values of $RH_{sensor}$, $T_s$, and $T_h$. It is within the scope of the disclosure for other controllers, microprocessors, memory and or discrete components to be used to perform correlation.

Implementation of sensor module 10 with incubator 26 is achieved by properly calibrating thermistors 37–40 and humidity chip 36 in a known fashion to provide accurate analog signals representative of the quantities being measured. These analog signals are then converted to digital signals by A/D converter 88. While shown diagrammatically as a single box, A/D converter 88 may include a plurality of dedicated converters or a single converter and switching mechanisms for selecting the analog signal to be converted to a digital signal.

As previously described, the humidity sensor 36 of the illustrated embodiment outputs an analog signal (RH) having a value between zero and one volt DC indicating a relative humidity at the sensor ($RH_{sensor}$) of between 0–100%. Op-amp 70, having a gain of X4, amplifies the RH signal to generate HS2 signal having a value of between zero and four volts indicating a relative humidity at the sensor ($RH_{sensor}$) of between 0–100%. A/D converter 88 converts an analog 0–5 V DC signal to a digital signal having 0–4095 counts. The HS2 signal (having a maximum value at 100% relative humidity of 4 V DC) is converted by A/D converter 88 to generate a digital representation of the $RH_{sensor}$ having a value between 0 and 3276 counts. This digital representation of $RH_{sensor}$ is made available to correlator 86. In the illustrated embodiment, $RH_{sensor}$ is either accessed directly by microprocessor 92 or stored in memory 90 for later access by microprocessor 92.

The analog signals affected by thermistors 37–40 are likewise converted by A/D converter 88 to digital signals (represented by counts) indicative of $T_s$ and $T_h$. In the illustrated embodiment, implementation requires the initial step of relating temperature to counts. For the temperature range of 15C to 55C data was generated relating counts with a given temperature using the Steinhart and Hart equation set forth above.

In the illustrated embodiment, because of the limitations of the micro-controller used, implementation involved creating a relationship between temperature (T) and saturated vapor pressure ($P_{vp}$) so that the program implemented by correlator 86 could be simplified. For the temperature range of 15C to 55C data was generated relating saturated vapor pressure ($P_{vp}$) to temperature (T) using the modified Clausius Clayperon Equation set forth above.

The data of step 1 and step 2 were combined to generate a relationship between counts and saturated vapor pressure ($P_{vp}$). The incremental counts were treated as an x-variable and the saturation vapor pressure ($P_{vp}$) was treated as a y-variable to generate the relationship of counts to saturation vapor pressure ($P_{vp}$).

In a fourth step the data from the third step relating counts to saturation vapor pressure ($P_{vp}$) was fitted to a curve to generate a polynomial equation relating counts to saturation vapor pressure ($P_{vp}$). Many curve fitting programs are available which may be used to generate an equation relating counts to saturation vapor pressure ($P_{vp}$). In implementing the illustrated embodiment, the data from step 3 was input into TableCurve™ available from SPSS Science, 233 S. Wacker Drive, Chicago, Ill., which generated the following fourth order polynomial equation relating counts ($counts_{temp}$) to saturation vapor pressure ($P_{vp}$):

$$P_{vp} = a + b \cdot counts_{temp} + c \cdot counts_{temp}^2 + d \cdot counts_{temp}^3$$

where a=1.5811294, b=−0.11519434, c=3.7242672×10⁻⁵, and d=−4.6847637×10⁻⁹.

Having established a relationship between saturation vapor pressure ($P_{vp}$) and the digitally converted signal from a thermistor, and having established a relationship between the relative humidity at the sensor ($RH_{sensor}$) and the amplified and digitally converted signal from the humidity sensor 36, the actual relative humidity in the interior of the incubator ($RH_{hood}$) is calculated by the correlator 86 using the following equation:

$$RH_{hood} = RH_{sensor} \cdot \left( \frac{a + b \cdot counts_{s\_temp} + c \cdot counts_{s\_temp}^2 + d \cdot counts_{s\_temp}^3}{a + b \cdot counts_{h\_temp} + c \cdot counts_{h\_temp}^2 + d \cdot counts_{h\_temp}^3} \right)$$

where $counts_{s\_temp}$ is the counts generated by the digitally converted signal from secondary thermistor 40 and $counts_{h\_temp}$ is the counts generated by the digitally converted signal from primary thermistors 37–39. Since $RH_{sensor}$ is represented by between 0 and 3276 counts and $counts_{s\_temp}$ is equal to or higher than $counts_{h\_temp}$, $RH_{hood}$ is a digital signal between 0 and 3276 counts representing 0–100% relative humidity ($RH_{hood}$) in the interior 24 of incubator 26. However, since the host system 54 of incubator 26 only accepts digital data represented by between 0–1600 counts, correlator 86 scales $RH_{hood}$ by a scaling factor of 0.488400488 for proper interfacing with host system 54. Host system 54 then uses $RH_{hood}$ data to control and/or display the relative humidity in the interior 24 of incubator 26 in a known manner.

Illustratively therefore, the described correlator 86 adjusts the indication of relative humidity adjacent the humidity sensor to provide an indication of the relative humidity within the incubator. Those skilled in the art will recognize that the adjusted relative humidity signal can then be used by a controller in system host 54 to properly control relative humidity within the hood 13 of incubator 26.

The illustrated sensor module 10 has an air inlet 44 opening into interior 24 of hood 13 of incubator 26, and a humidity sensor 36 spaced apart from the air inlet 44 for providing an indication of the relative humidity of the air adjacent the humidity sensor 36. A first temperature sensor 37–39 is mounted adjacent the air inlet opening 44 to provide an indication of the air temperature within the interior 24 of hood 13 of incubator 26. Second temperature sensor 40 is mounted adjacent humidity sensor 36 to provide an indication of the air temperature adjacent the humidity sensor 36. A correlator 86 in communication with the humidity sensor 36, first temperature sensor 37–39, and second temperature sensor 40 provides an indication of the relative humidity within the interior 24 of hood 13 of incubator. It is within the teaching of the current disclosure for first temperature sensor 37–39 to be located within interior 24 of hood 13 of incubator 26 or at another location wherein first temperature sensor 37–39 senses air at a temperature approximately equal to the temperature of the air within the interior 24 of hood 13 of incubator 26. It is also within the teaching of the disclosure for humidity sensor and second temperature sensor 40 to be located remotely from first temperature sensor 37–39 at a position where air withdrawn from the interior 24 of hood 13 of incubator 26 may be sensed.

Figure 10:
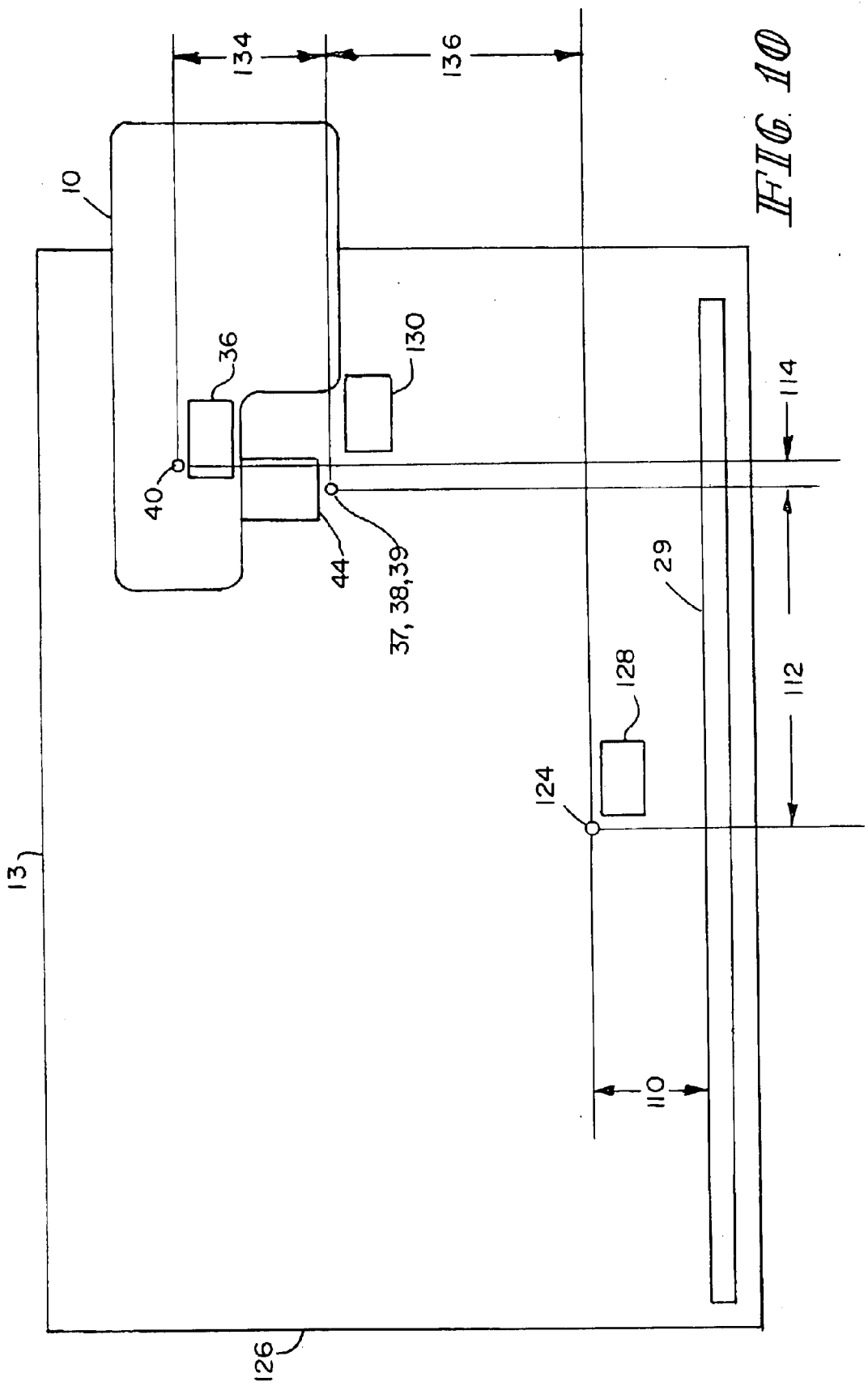
FIG. 10 is a diagrammatic view of a sensor module incorporated into a hood of an infant support containing a mattress and additional temperature and relative humidity sensors used to compensate for temperature and relative humidity differentials which may be present between the center of the mattress and the inlet of the sensor module.
Figure 11:
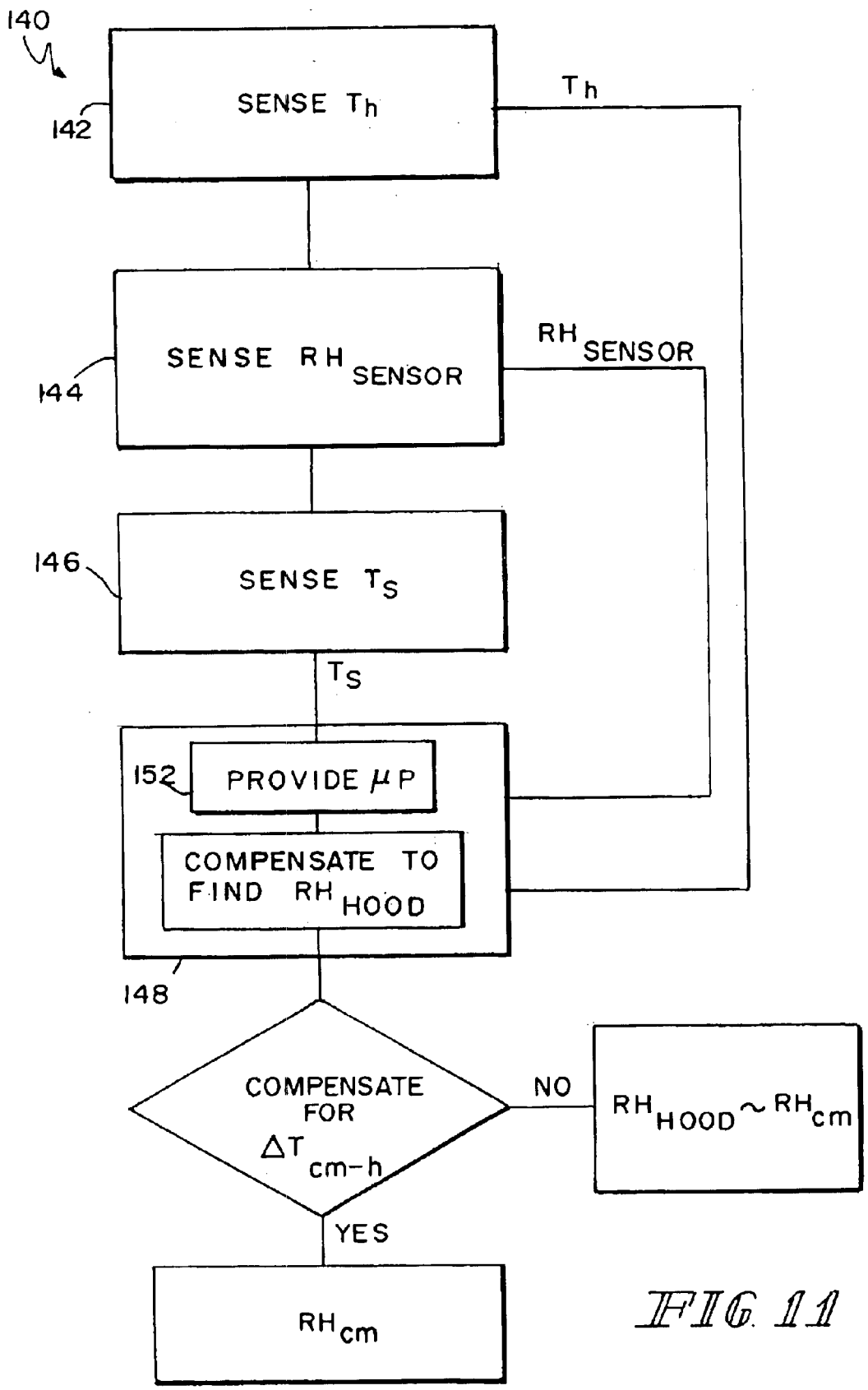
FIG. 11 is a flow chart of a method of sensing relative humidity within an enclosure.

FIG. 10 is a diagrammatic view of the hood 13, mattress 29 and sensor module 10 of the illustrated embodiment. Those skilled in the art will recognize that an infant received within hood will typically be exposed directly to air at distance 110 approximately 10 centimeters above the center of the mattress, such point being hereinafter referred to as "center mattress". In the illustrated embodiment, it has been found that the temperature of the air at center mattress $T_{cm}$ may differ from the temperature of the air at inlet $T_h$ by temperature difference $\Delta T_{cm-h}$ 112 approximately 1.6 degrees C. This compares to a typical temperature differential $\Delta T_{h-s}$ 114 of approximately 4 degrees C. between the air at inlet 44 ($T_h$) and the air at humidity sensor 36 ($T_s$). In the illustrated embodiment $\Delta T_{cm-h}$ is relatively small compared to $\Delta T_{h-s}$. Thus, the relative humidity of the air adjacent the infant $RH_{cm}$ is approximately equal to the correlated relative humidity $RH_{hood}$ generated by sensor module 10.

When sensor module 10 is installed in other infant support devices, the air temperature differential $\Delta T_{cm-h}$ 112 between center mattress and inlet 44 may be substantially higher than that exhibited in the illustrated embodiment. $RH_{hood}$ can be further adjusted to more accurately reflect $RH_{cm}$ within the scope of the disclosure. Such further adjustment of $RH_{hood}$ could be desirable if an even more accurate indication of the relative humidity of the air adjacent the infant ($RH_{cm}$) is desired in the illustrated embodiment or if temperature differentials $\Delta T_{cm-h}$ 112 between the air at the center of the mattress ($T_{cm}$) and the air at inlet ($T_h$) in an infant support into which sensor module 10 is incorporated is large enough to adversely affect the approximation of $RH_{cm}$ by the correlated $RH_{hood}$. Since the necessary adjustment may differ depending on the type of infant support into which sensor module 10 is incorporated, it is preferable that such adjustment be implemented by the host system 54 of the support device 126 which would then act as a part of correlator 86. However, it is within the teaching of the disclosure for the $RH_{hood}$ to $RH_{cm}$ adjustment to be implemented by microprocessor 92 within module 10, a separate processor, or other devices either within or remotely located from sensor module 10.

This additional compensation to adjust $RH_{hood}$ to more accurately reflect $RH_{cm}$ is illustratively performed during calibration of sensor module 10 and infant support device 126. During calibration, additional properly calibrated temperature sensor 124 and humidity sensors 128 and 130 are positioned within hood 13. Temperature sensor 124 and humidity sensor 128 are positioned at center mattress and humidity sensor 130 is positioned adjacent air inlet 44 as shown, for example, in FIG. 10. Humidity sensors 128, 130 are calibrated by placing the same in a saturated LiCl and NaCl solution.

This additional compensation uses the Modified Clausius Clayperon Equation disclosed above. To determine actual relative humidity at center mattress $RH_{cm}$, the following equation is used to relate $RH_{cm}$ to the relative humidity correlated by sensor module $RH_{hood}$ based on the air temperature measured by second thermistor 40 $T_s$ and additional thermistor 124 $T_{cm}$.

$$RH_{cm} = RH_{hood} * \frac{P_{vphood}}{P_{vpcm}}$$

To determine the relative humidity at center mattress $RH_{cm}$ it is necessary to measure the temperature $T_{cm}$ at center mattress using thermistor 124. From the system temperature design and comparison of temperature data collected from first thermistors 37, 38, 39 and thermistor 124 the required offset temperature $T_{offset}$ can be determined. From data collected from the illustrated embodiment, the appropriate offset temperature $T_{offset}$ was determined. By using thermistor 124 and thermistors 37, 38, 39 it was determined that the appropriate offset $T_{offset}$ for the illustrated embodiment was 0.5 degrees C. Those skilled in the art will recognize that $T_{offset}$ will vary depending on the device 126 into which sensor module 10 is incorporated. The calculated offset is added to, or subtracted from the sensor module's hood air temperature measurement $T_h$. Using this fixed value, it's easy to find the center mattress relative humidity using only the sensors 36, 37, 38, 39, 49 in sensor module 10. Since sensors 37, 38, 39 determine the temperature $T_h$ at inlet 44, the temperature at center mattress $T_{cm}$ can be calculated by adding the temperature offset $T_{offset}$ to the temperature sensed at the inlet 44 $T_h$. Thus, $T_{cm}=T_h+T_{offset}$. Then using the Modified Clausius Clayperon Equation to find $P_{vp}(T)$ the center mattress relative humidity is determined by applying:

$$RH_{cm} = RH_{hood} * \frac{P_{vp}(T_h)}{P_{vp}(T_{cm})}$$

The air temperature measurement (without any offset correction implemented) from the sensor module $T_h$ (in Degrees C.) is plugged into the Modified Clausius Clayperon Equation to determine sensor module saturation vapor pressure. The air temperature measurement from the sensor module (with offset correction added in) is plugged into the Modified Clausius Clayperon Equation to determine center mattress saturation vapor pressure. The ratio of sensor module saturation vapor pressure to center mattress saturation vapor pressure is calculated and multiplied by the relative humidity from the sensor module ($RH_{hood}$) to determine the center mattress relative humidity $RH_{cm}$. Thus, in the illustrated embodiment the relative humidity differential $\Delta RH_{hood-s}$ 134 between the relative humidity at inlet 44 $RH_{hood}$ and the relative humidity sensed by sensor 36 $RH_s$ is compensated for in sensor module 10 by correlator 86, while the relative humidity differential $\Delta RHcm-_{hood}$ 136 between the relative humidity at inlet 44 $RH_{hood}$ and the relative humidity at center mattress $RH_{cm}$ is compensated for in host system 54 of infant support 126 acting as a portion of correlator 86. The compensation for the relative humidity differential $\Delta RHcm-_{hood}$ 136 between the relative humidity at inlet 44 $RH_{hood}$ and the relative humidity at center mattress $RH_{cm}$ may be carried out by microprocessor 92 within sensor module 10, be carried out by a separate processor or device, or not carried out at all within the scope of the disclosure.

A method 140 for determining the humidity of the air surrounding an infant in an infant care enclosure comprises the steps of sensing the temperature of the air in the enclosure 142 with a first temperature sensor, sensing humidity of the air at a point spaced from the infant 144, sensing the air temperature at the point where the humidity is sensed 146 with a second temperature sensor, and correlating the temperature sensed by first and second temperature sensors and the humidity sensed to determine the humidity of the air surrounding the infant 148. This method 140 of determining the relative humidity of the air surrounding the infant may be carried out using the disclosed sensor module 10 or stand alone temperature sensors and humidity sensors within the scope of this disclosure. Additionally, $RH_{hood}$ can be compensated to adjust for the difference between the temperature at center mattress $T_{cm}$ and the temperature sensed by the first temperature sensor $T_h$ 150 to adjust for temperature differentials between the temperature of the air surrounding the infant and the temperature of the air at the location within the enclosure where the first sensor is located. A microprocessor may be provided 152 which communicates with the first temperature sensor, a humidity sensor sensing the humidity and the second temperature sensor to perform the adjustment based on mathematical models.

Although the invention has been described in detail with reference to preferred embodiments, variations and modification exist within the scope and spirit of the invention as described.

What is claimed is:

1. A temperature and humidity sensing module for use with an infant care enclosure of an incubator, the module having an inlet configured to receive air from the enclosure, a primary temperature sensor to sense the air received in the module, a humidity sensor disposed in the module to sense the humidity of the air received therein, and a second temperature sensor within the module and located adjacent the humidity sensor to determine the temperature of the air at the point the humidity of the air is sensed.

2. The apparatus of claim 1 wherein the module comprises a housing having a chamber within which the humidity sensor and second temperature sensor are received.

3. The apparatus of claim 1 further comprising a blower positioned to move air between the enclosure and the module.

4. The apparatus of claim 3 wherein the blower is a fan.

5. The apparatus of claim 3 wherein the module comprises a housing having a chamber within which the humidity sensor and second sensor are received.

6. The apparatus of claim 5 wherein the housing is formed to include said inlet and an exhaust portal and the humidity sensor is positioned within the housing between said inlet and the exhaust portal.

7. The apparatus of claim 1, further comprising a correlator operatively coupled to the primary temperature sensor, humidity sensor, and second temperature sensor, the correlator configured to determine the humidity of air within the infant care enclosure in response to the temperature of the air received in the module, the humidity of the air received therein, and the temperature of the air at the point the humidity of the air is sensed.

8. A temperature and humidity sensing module for an infant care enclosure, the module having an inlet configured to receive air from the enclosure, a primary temperature sensor to sense the air received in the module, a humidity sensor disposed in the module to sense the humidity of the air received therein, a second temperature sensor within the module to determine the temperature of the air at the point the humidity of the air is sensed, and a blower positioned to move air between the enclosure and the module, the module comprising a housing having a chamber within which the humidity sensor and second sensor are received, the housing being formed to include said inlet and an exhaust portal, the humidity sensor being positioned within the housing between said inlet and the exhaust portal, the blower is being positioned within the housing between the humidity sensor and the exhaust portal.

9. The apparatus of claim 8 wherein the primary temperature sensor is positioned within the housing adjacent said inlet.

10. A method for determining the humidity of the air at the position an infant rests in an enclosure by drawing air from the enclosure past a humidity sensor spaced apart from the infant, sensing the temperature of the air drawn from the enclosure, sensing the temperature of the air adjacent the humidity sensor, and correlating the temperature sensed and humidity sensed to determine the humidity adjacent the infant.

11. A method for determining the humidity of the air surrounding an infant in an infant care enclosure comprising the steps of sensing the temperature of the air in the enclosure with a first temperature sensor, sensing humidity of the air at a point spaced from the infant, sensing the temperature at the point where the humidity is sensed with a second temperature sensor, and correlating the temperature sensed by first and second temperature sensors and the humidity sensed to determine the humidity of the air surrounding the infant.

12. A humidity sensing assembly for an incubator, the humidity sensing assembly comprising a first temperature sensor sensing the temperature of air within the incubator, and a module cooperating with the first temperature sensor to provide an indication of the humidity of the air within the incubator, the module comprising a humidity sensor sensing the humidity of the air within the module, and a second temperature sensor sensing the temperature of air adjacent the humidity sensor.

13. The assembly of claim 12, wherein the module further composes a housing including a shell defining an interior region of the housing, the humidity sensor and the second temperature sensor being received by the interior region of the housing.

14. The assembly of claim 12, further comprising a correlator operatively coupled to the humidity sensor and the first and second temperature sensors and configured to determine the humidity of air within the incubator in response thereto.

15. The assembly of claim 12, wherein the module further includes a correlator operatively coupled to the second temperature sensor and to the humidity sensor, the first temperature sensor being operatively coupled to the correlator, the correlator being configured to determine the humidity of air within the incubator in response to the temperature of the air within the incubator, the humidity of the air within the module, and the temperature of the air adjacent the humidity sensor.

16. The assembly of claim 15, wherein the module further comprises a housing including a shell defining an interior region of the housing, the humidity sensor and the second temperature sensor being received by the interior region of the housing.

17. A system for determining the humidity of air surrounding an infant in an infant care device, the system comprising a first temperature sensor positioned to sense the temperature of the air surrounding the infant and providing a first temperature signal in response thereto, a humidity sensor configured to sense the humidity of the air surrounding the infant and providing a first humidity signal in response thereto, a second temperature sensor positioned to sense the temperature of the air adjacent the humidity sensor and providing a second temperature signal in response thereto, and a correlator configured to determine the humidity of the air surrounding the infant in response to the first humidity signal and the first and second temperature signals.

18. The system of claim 17, wherein the correlator includes a circuit providing a calculated humidity signal in response to the first humidity signal and to the first and second temperature signals.

19. The system of claim 17, further comprising a display operatively coupled to the correlator and configured to provide a visual indication of the humidity of the air surrounding the infant in response to the calculated humidity signal.

20. A temperature and humidity sensing module for an infant care enclosure, the module comprising a housing having an inlet port and an exhaust port, a blower for moving air from the enclosure through the housing, a primary temperature sensor within the housing for determining the temperature of the air drawn into the inlet port, a humidity sensor within the housing for determining the humidity of the air drawn into the housing, and a secondary temperature sensor within the housing and located adjacent the humidity sensor to determine the temperature of the air at the point the humidity is sensed.

21. The apparatus of claim 20, further comprising a correlator configured to determine the humidity of the air surrounding the infant in response to the temperature sensed by the primary and secondary temperature sensors and the humidity sensed by the humidity sensor.

* * * * *